(12) United States Patent
Gorhan et al.

(10) Patent No.: US 9,226,775 B2
(45) Date of Patent: *Jan. 5, 2016

(54) LOCKING BONE SCREW AND SPINAL PLATE SYSTEM

(71) Applicant: DePuy Synthes Products, Inc., Raynham, MA (US)

(72) Inventors: Michael Gorhan, Mansfield, MA (US); Michael Jacene, Blackstone, MA (US); Eric D. Kolb, Sandy Hook, CT (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/891,471

(22) Filed: May 10, 2013

(65) Prior Publication Data

US 2013/0282065 A1 Oct. 24, 2013

Related U.S. Application Data

(63) Continuation of application No. 13/070,833, filed on Mar. 24, 2011, now Pat. No. 8,460,348, which is a continuation of application No. 10/904,992, filed on Dec. 8, 2004, now Pat. No. 7,935,137.

(51) Int. Cl.
*A61B 17/04* (2006.01)
*A61B 17/86* (2006.01)
(Continued)

(52) U.S. Cl.
CPC ........... *A61B 17/685* (2013.01); *A61B 17/8038* (2013.01); *A61B 17/8615* (2013.01); *A61B 17/8685* (2013.01); *A61B 17/888* (2013.01); *A61B 17/7059* (2013.01); *A61B 17/8894* (2013.01); *A61B 2017/00004* (2013.01); *A61B 2019/305* (2013.01); *A61B 2019/446* (2013.01)

(58) Field of Classification Search
USPC .................. 606/300–302, 305–308, 314, 319, 606/286–295
See application file for complete search history.

(56) References Cited

U.S. PATENT DOCUMENTS 4,026,187 A 5/1977 Gross
5,364,399 A 11/1994 Lowery et al.
(Continued)

FOREIGN PATENT DOCUMENTS

EP 1 306 058 A2 5/2003
WO 03/103507 A2 12/2003
WO 2006/040063 A1 4/2006

OTHER PUBLICATIONS

European Search Report, Application No. 05825655.3, Mailed Jul. 6, 2009, 15 pages.
(Continued)

*Primary Examiner* — Sameh Boles
(74) *Attorney, Agent, or Firm* — Nutter McClennen & Fish LLP

(57) ABSTRACT

A bone plate system including a bone plate and a bone screw with an integrated locking mechanism is disclosed. The bone screw includes an elongate member having a threaded shank and a bone screw head that is radially deformable. The integrated locking mechanism sits within the bone screw head and can rotate between a locked condition and an unlocked condition. When the bone screw head is seated within an aperture in the bone plate, rotating the integrated locking mechanism into the locked condition helps to prevent bone screw backout.

19 Claims, 8 Drawing Sheets

(51) Int. Cl.
*A61F 2/08* (2006.01)
*A61B 17/68* (2006.01)
*A61B 17/80* (2006.01)
*A61B 17/88* (2006.01)
*A61B 17/70* (2006.01)
*A61B 17/00* (2006.01)
*A61B 19/00* (2006.01)

(56) References Cited

U.S. PATENT DOCUMENTS

| | | | |
|---|---|---|---|
| 5,520,690 A | 5/1996 | Errico et al. | |
| 5,534,027 A | 7/1996 | Hodorek | |
| 5,578,034 A | 11/1996 | Estes | |
| 5,683,390 A * | 11/1997 | Metz-Stavenhagen et al. | 606/278 |
| 5,713,900 A | 2/1998 | Benzel et al. | |
| 5,735,853 A | 4/1998 | Olerud | |
| 5,876,402 A | 3/1999 | Errico et al. | |
| 5,902,303 A | 5/1999 | Eckhof et al. | |
| 5,904,683 A | 5/1999 | Pohndorf et al. | |
| 5,931,838 A | 8/1999 | Vito | |
| 5,954,722 A | 9/1999 | Bono | |
| 5,957,953 A | 9/1999 | DiPoto et al. | |
| 6,039,740 A | 3/2000 | Olerud | |
| 6,206,882 B1 | 3/2001 | Cohen | |
| 6,235,033 B1 | 5/2001 | Brace et al. | |
| 6,241,731 B1 | 6/2001 | Fiz | |
| 6,261,291 B1 | 7/2001 | Talaber et al. | |
| 6,331,179 B1 | 12/2001 | Freid et al. | |
| 6,428,542 B1 | 8/2002 | Michelson | |
| 6,454,769 B2 | 9/2002 | Wagner et al. | |
| 6,554,834 B1 | 4/2003 | Crozet et al. | |
| 6,575,975 B2 | 6/2003 | Brace et al. | |
| 6,595,993 B2 | 7/2003 | Donno et al. | |
| 6,599,290 B2 | 7/2003 | Bailey et al. | |
| 6,602,255 B1 | 8/2003 | Campbell et al. | |
| 6,656,181 B2 | 12/2003 | Dixon et al. | |
| 6,679,883 B2 | 1/2004 | Hawkes et al. | |
| 6,695,845 B2 | 2/2004 | Dixon et al. | |
| 6,695,846 B2 | 2/2004 | Richelsoph et al. | |
| 6,890,334 B2 | 5/2005 | Brace et al. | |
| 6,945,975 B2 | 9/2005 | Dalton | |
| 6,964,664 B2 | 11/2005 | Freid et al. | |
| 6,979,334 B2 | 12/2005 | Dalton | |
| 7,001,389 B1 | 2/2006 | Navarro et al. | |
| 7,048,739 B2 | 5/2006 | Konieczynski et al. | |
| 7,063,701 B2 | 6/2006 | Michelson | |
| 7,273,481 B2 | 9/2007 | Lombardo et al. | |
| 7,780,703 B2 * | 8/2010 | Yuan et al. | 606/246 |
| 7,846,190 B2 * | 12/2010 | Ball | 606/313 |
| 7,935,137 B2 | 5/2011 | Gorhan et al. | |
| 8,162,989 B2 * | 4/2012 | Khalili | 606/266 |
| 2001/0014807 A1 | 8/2001 | Wagner et al. | |
| 2001/0037112 A1 | 11/2001 | Brace et al. | |
| 2002/0016595 A1 | 2/2002 | Michelson | |
| 2002/0045898 A1 | 4/2002 | Freid et al. | |
| 2002/0058939 A1 | 5/2002 | Wagner et al. | |
| 2002/0151899 A1 | 10/2002 | Bailey et al. | |
| 2003/0078583 A1 | 4/2003 | Biedermann et al. | |
| 2003/0083658 A1 | 5/2003 | Hawkes et al. | |
| 2003/0105462 A1 | 6/2003 | Haider | |
| 2003/0171754 A1 | 9/2003 | Del Medico | |
| 2003/0187440 A1 | 10/2003 | Richelsoph et al. | |
| 2003/0187442 A1 | 10/2003 | Richelsoph et al. | |
| 2003/0199876 A1 | 10/2003 | Brace et al. | |
| 2003/0208204 A1 | 11/2003 | Bailey et al. | |
| 2003/0225409 A1 | 12/2003 | Freid et al. | |
| 2004/0019353 A1 | 1/2004 | Freid et al. | |
| 2004/0087951 A1 | 5/2004 | Khalili | |
| 2004/0097935 A1 | 5/2004 | Richelsoph et al. | |
| 2004/0127896 A1 | 7/2004 | Lombardo et al. | |
| 2004/0127897 A1 | 7/2004 | Freid et al. | |
| 2004/0127899 A1 | 7/2004 | Konieczynski et al. | |
| 2004/0127900 A1 | 7/2004 | Konieczynski et al. | |
| 2004/0127904 A1 | 7/2004 | Konieczynski et al. | |
| 2004/0181227 A1 | 9/2004 | Khalili | |
| 2005/0010218 A1 | 1/2005 | Dalton | |
| 2005/0010219 A1 | 1/2005 | Dalton | |
| 2005/0049593 A1 | 3/2005 | Duong et al. | |
| 2005/0149027 A1 | 7/2005 | Campbell et al. | |
| 2005/0228386 A1 | 10/2005 | Ziolo et al. | |
| 2005/0251137 A1 | 11/2005 | Ball | |
| 2005/0267474 A1 | 12/2005 | Dalton | |
| 2005/0273105 A1 | 12/2005 | Konieczynski et al. | |
| 2006/0015104 A1 | 1/2006 | Dalton | |
| 2006/0100626 A1 | 5/2006 | Rathbun et al. | |
| 2006/0122604 A1 | 6/2006 | Gorhan et al. | |
| 2011/0172719 A1 | 7/2011 | Gorhan et al. | |

OTHER PUBLICATIONS

Foley, K., et al., Percutaneous pedicles screw fixation of the lumber spine. Neurosurg Focus Apr. 15, 2001;10(4):E10.

Keller, M.A., et al., "The ComPact UniLock 2.0/2.4 systems and its clinical application in small animal orthopeics," Vet Comp Orthop Traumatol. 2005;18(2):83-93.

Lehmann, W., et al., "Biomechanical comparison of anterior cervical spine locked and unlocked plate-fixation systems," Eur Spine J. Apr. 2005;14(3):243-9. Epub Jun. 10, 2004.

Spivak, J., et al., "The Effect of Locking Fixation Screws on the Stability of Anterior Cervical Plating," Spine Feb. 15, 1999;24(4):334-8.

Yang, S. & Wang, L., "Biomechanical comparison of the stable efficacy of two anterior plating systems," Clin Biomech (Bristol, Avon). Jul. 2003;18(6):S59-66.

* cited by examiner

LOCKING BONE SCREW AND SPINAL PLATE SYSTEM

FIELD

The present invention relates to fixation devices used in orthopaedic and spinal surgery and particularly to bone fixation plate systems that include locking bone screws to prevent bone screw backout.

BACKGROUND

For a number of known reasons, bone fixation devices are useful for promoting proper healing of injured or damaged vertebral bone segments caused by trauma, tumor growth, or degenerative disc disease. The fixation devices immobilize the injured bone segments to ensure the proper growth of new osseous tissue between the damaged segments. These types of bone fixation devices often include internal bracing and instrumentation to stabilize the spinal column to facilitate the efficient healing of the damaged area without deformity or instability, while minimizing any immobilization and post-operative care of the patient.

One such device is an osteosynthesis plate, more commonly referred to as a bone fixation plate, that can be used to immobilize adjacent skeletal parts such as bones. Typically, the fixation plate is a rigid metal or polymeric plate positioned to span bones or bone segments that require immobilization with respect to one another. The plate is fastened to the respective bones, usually with bone screws, so that the plate remains in contact with the bones and fixes them in a desired position. Bone plates can be useful in providing the mechanical support necessary to keep vertebral bodies in proper position and bridge a weakened or diseased area such as when a disc, vertebral body or fragment has been removed.

It is known that in bone plate systems in general, and in those systems used for stabilization of the spinal column in particular, a loosening of the bone screws which secure the bone plate to the bone segment can occur. When the bone screws become loose, they may move in an axial direction (i.e., screw back out may occur).

Conventional bone plate systems offer several options for securing the bone screws to the bone plate and preventing screw backout. For example, some systems rely on split rings positioned between the bone screw and the bone plate; other system use bone screw covers that are mated to the bone plate in a position above an implanted bone screw; and still other systems use a locking screw that is driven into the top of an implanted bone screw. Despite the existence of these bone plate systems, there remains a need for an effective bone screw locking mechanism that can be installed and actuated with ease and efficiency.

SUMMARY

Disclosed herein is a bone screw with an integrated locking mechanism that helps to prevent bone screw backout after implantation. The bone screw and locking mechanism are effective and easy to use. In addition, the bone screw can be implanted and the locking mechanism engaged with a minimal number of steps. For example, the bone screw can be implanted and the locking mechanism engaged with the same tool.

In one embodiment, the bone screw comprises an elongate member having a threaded shank and a head at a proximal end thereof. The head, which is radially deformable, is defined by an outer wall that defines an inner hollow region. An inner surface of the outer wall has a circumferential groove that seats a screw locking mechanism. The screw locking mechanism can be rotated between a locked condition and an unlocked condition.

In one aspect, at least one axially oriented slot is formed in the outer surface of the head, extending distally from the proximal end of the screw. In an unlocked condition, locking features of the locking mechanism are aligned with the slot(s) to permit radial deformation of the head. In the locked position, the locking features abut the inner surface of the outer wall of the head to prevent radial deformation of the head.

At least a portion of the bone screw head has a spherically shaped outer surface that is interrupted by the axially oriented slots formed in the outer wall. The slots, as noted above, allow the bone screw head to deform, for example to reduce its diameter. The locking mechanism can have a substantially circularly shaped first portion that is adapted to be rotatably disposed within the seating groove, and a second portion, proximal to the first portion, that includes at least one locking feature adapted to engage the inner surface of the outer wall in a locked condition. In addition, the bone screw head can have a drive feature formed at a distal portion of the hollow region and the locking mechanism can have a drive feature formed in a central portion thereof. The drive features are adapted to mate with complementary drive elements on a driver tool.

In another aspect, a bone plate system includes at least one bone screw of the type noted above with an integrated locking mechanism, and a bone plate. The bone plate has a first surface, a second, bone-contacting surface opposed to the first surface, and at least one aperture extending through the first and second surfaces. The aperture has a predefined shape and size, and it is configured to seat a bone screw such that the head of the bone screw undergoes radial deformation, at least upon initial passage into the aperture.

At least a portion of the locking mechanism is rotatably disposed in the seating groove within the bone screw head such that the locking mechanism can be rotated relative to the bone screw between a locked condition and an unlocked conditions in one embodiment, the unlocked condition allows radial deformation of the head, and the locked condition prevents radial deformation of the head by way of a locking feature that abuts a portion of the inner surface of the outer wall.

The bone screw and locking mechanism each can include drive features. For example, the head of the bone screw can have a first drive feature formed at a distal portion of the hollow region and the locking mechanism can have a second drive feature. In one aspect, the first and second drive features are positioned coaxially with the first drive feature positioned distally to the second drive feature.

In one embodiment, the bone plate system includes a driver tool adapted to mate with the first and second drive features to implant the bone screw and to actuate the locking mechanism. The driver tool can include a proximal handle portion and a distal mating area that includes a first driver element adapted to mate with the first drive feature and a second driver element adapted to mate with the second drive feature. The proximal handle portion can include first and second handle portions capable of selective independent movement such that one handle can be rotated relative to the other. In one embodiment, the driver too can drive the bone screw into bone and subsequently the second drive feature can be independently rotated to actuate the locking mechanism without removing the tool.

BRIEF DESCRIPTION OF THE DRAWINGS

The invention can be more fully understood from the following detailed description taken in conjunction with the accompanying drawings, in which.

DETAILED DESCRIPTION OF THE EXEMPLARY EMBODIMENTS

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The following exemplary embodiments are described herein with reference to bone screws with bone plates that span and immobilize adjacent vertebral bodies in spinal fixation techniques. However, it is understood that the bone screws and bone plate systems described herein may be applicable to the fixation of any type of adjacent bones or bone segments.

Figure 1:
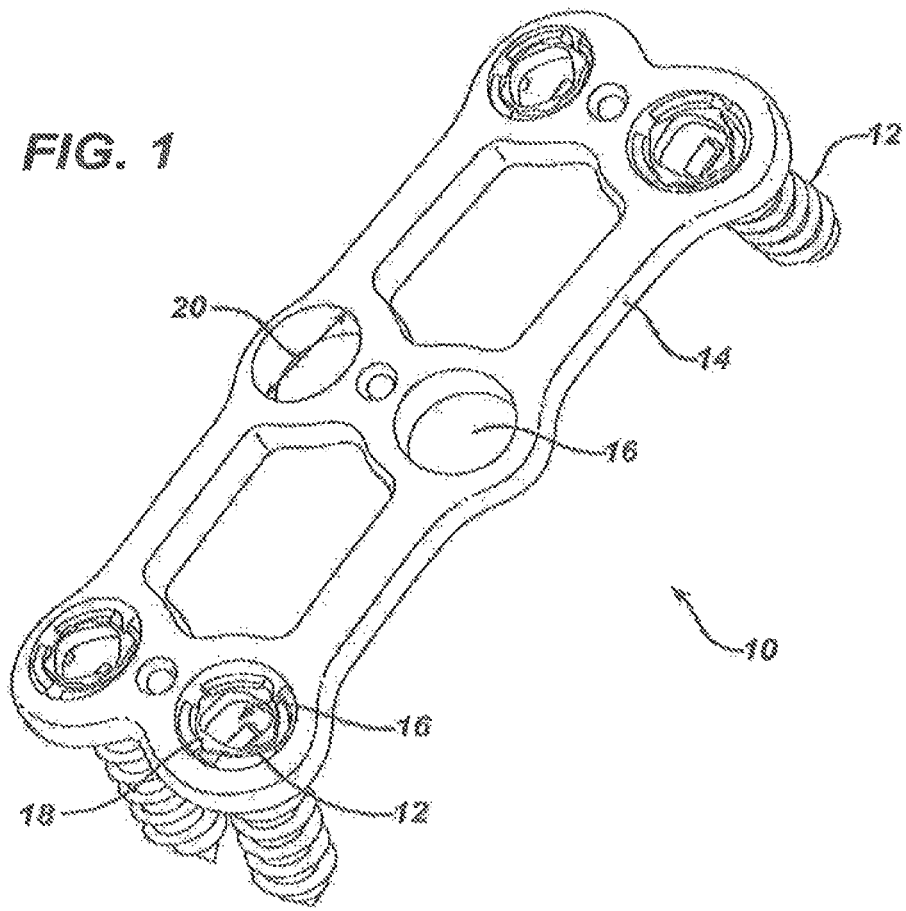
FIG. 1 is a perspective view of an exemplary embodiment of the bone plate system including a bone plate with bone screws having an integrated locking mechanism.

FIG. 1 illustrates one embodiment of the bone plate system 10 including bone screws 1 and bone plate 14 having apertures 16. Bone screws 12 are implanted through apertures 16 to fix bone plate 14 to bone (e.g., vertebral bodies). Each bone screw 12 includes a locking mechanism 18 that is movable between locked and unlocked positions. In the unlocked condition bone screw 12 is able to pass into an aperture within the plate and in the locked position the bone screw head is prevented from backing out of the aperture. The locking mechanism can be integrated (e.g., pre-assembled) within the screw head, or it can be assembled within the screw head on demand.

Bone screw 12 with locking mechanism 18 can be locked within a variety of bone plates that include apertures 16 having shapes and dimensions suitable to receive bone screw 12 and enable the bone screw to be locked therein. Exemplary plates include bone plates having an aperture 16 with an upper diameter 20 sized such that bone screw 12 with locking mechanism 18 in the locked condition is not able enter or exit though upper diameter 20.

Figure 2A:
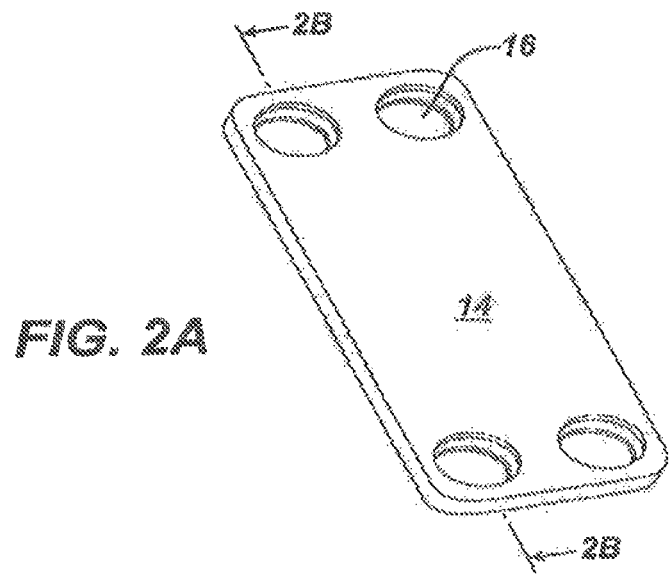
FIG. 2A is a perspective view of an embodiment of a bone plate useful with the present system.
Figure 2B:
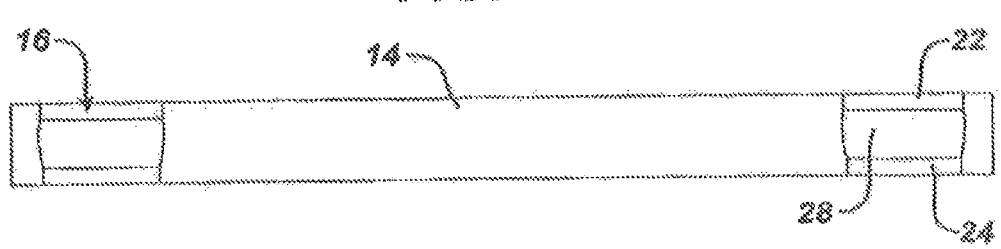
FIG. 2B is a sectional side view of the bone plate shown in FIG. 2A along lines 2B-2B.
Figure 2C:
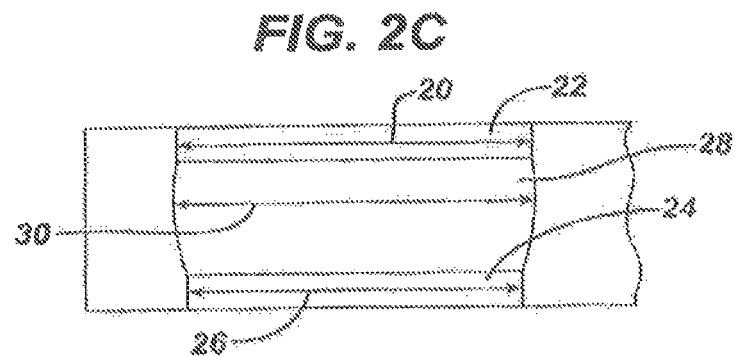
FIG. 2C is a partial, sectional side view of an aperture of the bone plate of FIG. 2A along lines 2B-2B.
Figure 2D:
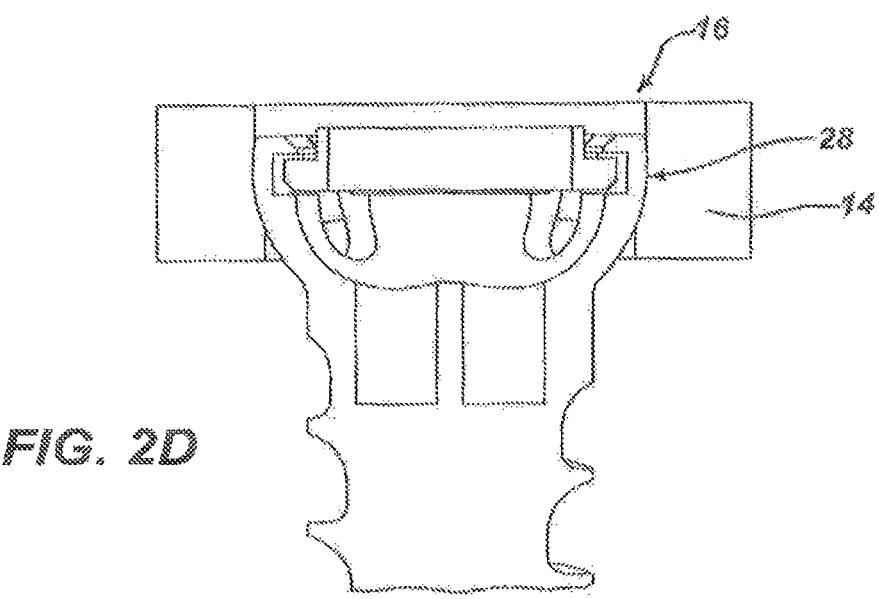
FIG. 2D is a sectional side view of a portion of a bone plate having a bone screw disposed therein.

FIGS. 2A and 2B illustrate one such exemplary bone plate 14. As shown in the sectional side view of bone plate 14 provided in FIGS. 2B and 2C, aperture 16 has a variable diameter. The upper portion 22 of aperture 16 can have an upper diameter 20 while the lower portion 24 includes a lower diameter 26. Positioned between the upper and lower portions 22, 24 is a central portion 28 with a central diameter 30 that is larger than the upper and lower diameters 20, 26. As shown in FIG. 2D, the bone screw head can be locked within the larger diameter central portion 28 of the bone screw aperture 16.

Figure 3:
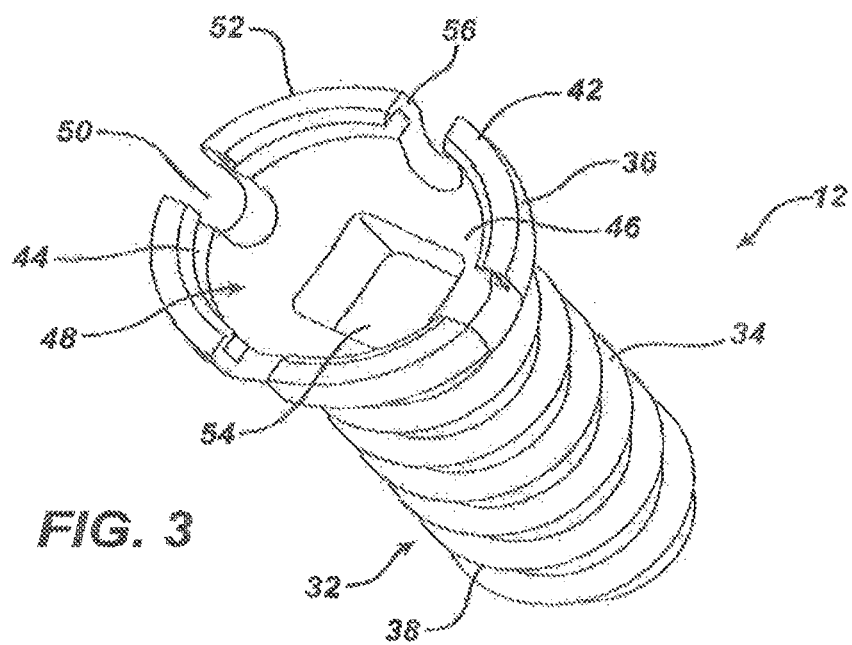
FIG. 3 is a perspective view of an embodiment of a bone screw useful with the system of FIG. 1.

FIG. 3 shows an exemplary bone screw 12 for positioning within aperture 16 that includes an elongate body 32 having a distal shank 34 and proximal head 36. The distal shank 34 can include threads 38 for fixing bone screw 12 to bone. A variety of bone screw threads adapted for fixing the bone screw and/or taping bone can be positioned on all or a portion of shank 34. In addition, one skilled hi the art will appreciate that a variety of thread patterns and sizes can be used.

Bone screw head 36 can have a variety of shapes including partially spherical, tapered, and irregularly shaped. In one embodiment, head 36 has a generally spherical shape corresponding to the shape of the central portion 30 of aperture 16. In another embodiment, the shape of head 36 includes a tapered top portion and a tapered bottom portion.

The head 36 of the bone screw 12 includes a wall 42, with an inner surface 44 and outer surface 46, that defines a hollow interior region 48. The bone screw head can be constructed in a variety of ways. In one embodiment, however, it should be able to deform radially.

In one aspect, the screw head is not able to fit within an aperture of the bone plate in its normal configuration. However, at least a portion of wall 42 is deformable, and the deformation enables the head of the screw to pass through and be seated in an aperture. For example, the wall 42 can be deflected inwardly when a compressive force (i.e., caused by passing the screw head through an aperture) is applied to the outer surface 46. Wall 42 may also be somewhat resilient such that after a compressive force is removed from the wall 42, the outer wall is able to return to its original shape and dimensions.

Generally, the bone screw head should be capable of deforming by a magnitude sufficient to allow it to fit within an aperture of a plate, for example, the outer diameter of the head can be reduced by approximately 0.001 to approximately 0.5 mm. The amount of deformation can dependent on the material(s) used to construct the bone screw and the type of structure into which the bone screw will be implanted. In one embodiment, the bone screw is a titanium bone screw sized for insertion into a cervical vertebra and the outer diameter of the head can be reduced by approximately 0.001 to approximately 0.25 mm.

To enable deformation, wall 42 can, in one embodiment, include axially oriented slots 50 to facilitate deformation of the head. As shown in FIG. 3, slots 50 can extend through wall 42 from the outer surface 46 to inner surface 44. In addition, the slots can extend distally from the proximal-most surface of the head through most of the height of outer wall 42 to define individually deflectable tabs 52. The space provided by slots 50 allows tabs 52 to deform (i.e., flex inwardly or outwardly) and to thereby alter the outer diameter of bone screw head 36 defined by wall 42. One skilled in the art will appreciate the width of the slots and the number of slots can vary depending on the desired amount of deflection in the outer wall. In one embodiment, however, four slots 50 are formed, thereby creating four tabs 52.

The hollow interior region 48 of bone screw head 36 can include additional features, such as a drive feature that is complementary with a driver element on a driver tool. For example, in the embodiment illustrated in FIG. 3, a drive feature 54 is positioned in the bottom surface of hollow interior region 48 in the form of a rectangularly shaped female drive feature. While the drive feature 54 illustrated in FIG. 3 is square, one skilled in the art will appreciate that it can have a variety of shapes capable of receiving a complementary driver element. For example, drive feature 54 can have other rectangular shapes or it can be triangular, hexagonal, oval, irregular, etc. In a further aspect, drive feature 54 could be a threaded female element that is able to receive a threaded male driver member. In addition, while the drive feature 54 is shown as a female socket, the drive feature 54 can be a male member that is capable of mating with a complementary female driver element.

The hollow interior region 48 of the bone screw head is also configured to receive an integrated screw locking mechanism 18. Inner surface 44 of the bone screw head 36 can have a variety of a mating features adapted to receive screw locking mechanism 18 and maintain the locking mechanism therein. In one aspect, the locking mechanism is seated within a mating feature during assembly of the bone screw. However, the locking mechanism could alternatively be positioned within the bone screw head by a user.

In one embodiment, the mating feature is a groove 56 that extends around the circumference of inner surface 44 to receive a portion of bone screw locking mechanism 18. One skilled in the art will appreciate that a variety of mating features, including, for example, grooves, threads, and/or raised features can be positioned with hollow interior region 48 for integrating the locking mechanism in bone screw head 36. In addition, as discussed below, multiple mating features can be disposed on inner surface 44.

Figure 4A:
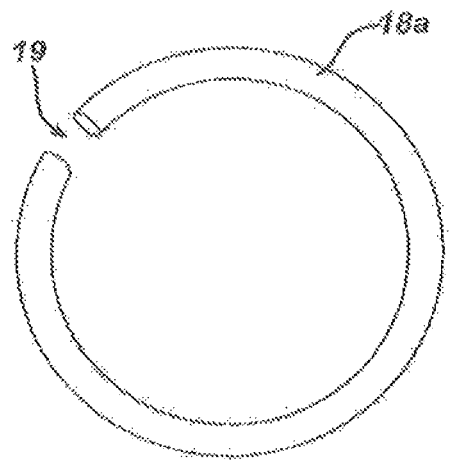
FIG. 4A is a perspective view of an embodiment of a locking mechanism that can be integrated within the bone screw described herein.
Figure 4B:
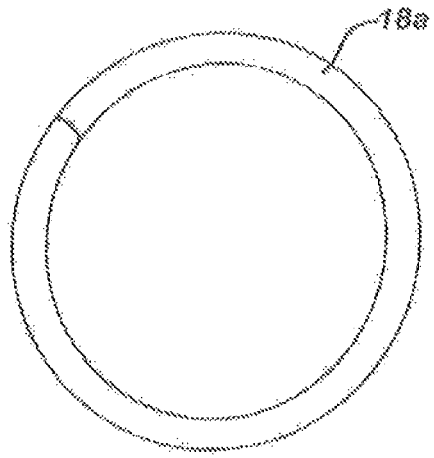
FIG. 4B is a perspective view of the locking mechanism of FIG. 4A in a locked condition.

A variety of locking mechanisms can sit within the mating feature(s) of the bone screw head 36 and be adapted to prevent deformation and/or to deform bone screw head 36. Exemplary locking mechanisms include disc-like locking mechanisms and locking rings. In one embodiment, locking mechanism 18a includes a split ring that sits in a first position when bone screw head 36 is in an unlocked condition and sits in a second position when bone screw head 36 is a locked condition. FIG. 4A illustrates locking mechanism 18a in an unlocked condition in which open space 19 allows the diameter of locking mechanism 18a to be reduced when a compressive force is applied. FIG. 4 shows locking mechanism 18a in a locked condition and space 19 closed such that the diameter of the locking mechanism cannot be further compressed.

Figure 4C:
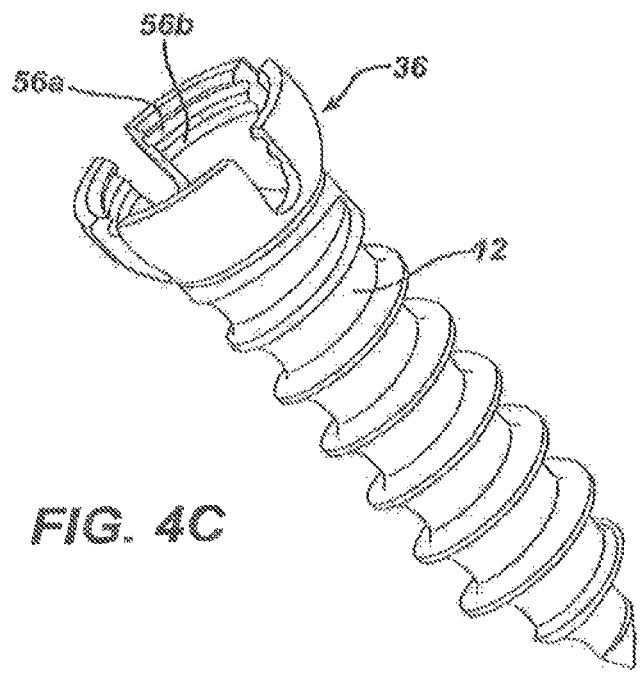
FIG. 4C is a perspective view of an embodiment of a bone screw adapted to receive the locking mechanism of FIGS. 4A and 4B.

The bone screw can have a variety of features suitable to seat a locking mechanism such as ring 18a. In one embodiment, inner surface 44 of bone screw head 36 can include two or more grooves adapted to receive split ring locking mechanism 18a. The inner surface 44, as shown in FIG. 4C, can include a first, proximal groove 56a and a second, distal groove 56b. In one embodiment, the proximal groove 56a has a larger diameter then the distal groove 56b such that when the locking mechanism is seated in groove 56a, the locking mechanism is in an unlocked condition (FIG. 4D), and when the locking mechanism is seated in groove 56b the locking mechanism is in a locked condition (FIG. 4E). Other useful features suitable to seat locking mechanism 18a include helical grooves and threads.

Figure 4D:
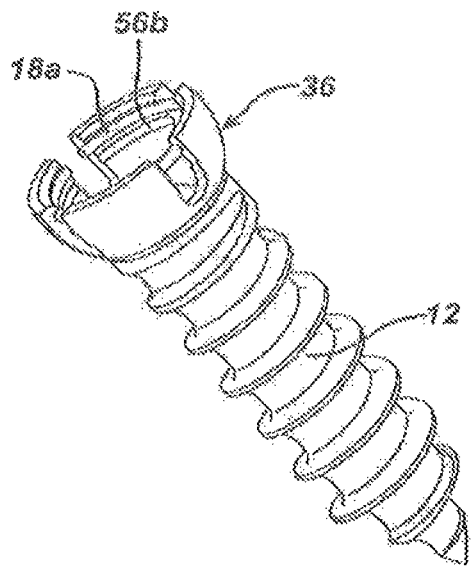
FIG. 4D is a perspective view of the bone screw of FIG. 4C with the locking mechanism of FIG. 4A integrated therein.
Figure 4E:
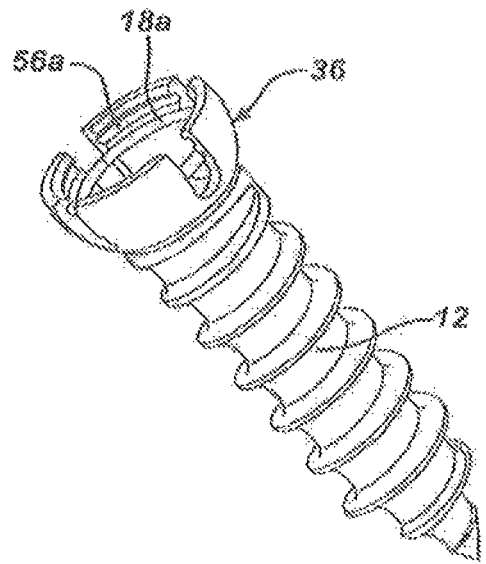
FIG. 4E is a perspective view of the bone screw and locking mechanism of FIG. 4D with the locking mechanism in a locked condition.

When the locking mechanism is in an unlocked condition, space 19 allows locking mechanism 18a to be compressed and tabs 52 to deflect inward to reduce the diameter of bone screw head 36 (FIG. 4D). However, when moved into groove 56b, locking mechanism 18a conforms to the smaller diameter of the groove and space 19 is dosed (or reduced). With space 19 dosed, the inability (or diminished ability) of locking mechanism 18a to further compress prevents tabs 52 from deforming. The bone screw head thus cannot be sufficiently deformed to allow passage through the upper diameter 20 of aperture 16.

Movement of locking mechanism 18a from groove 56a to 56b can be achieved by radially compressing locking mechanism 18a and moving the locking mechanism longitudinally. In an alternative embodiment, the interior surface 44 could be threaded (not shown), and the locking mechanism can be moved between a locked and unlocked condition by rotating the locking mechanism.

Figure 5A:
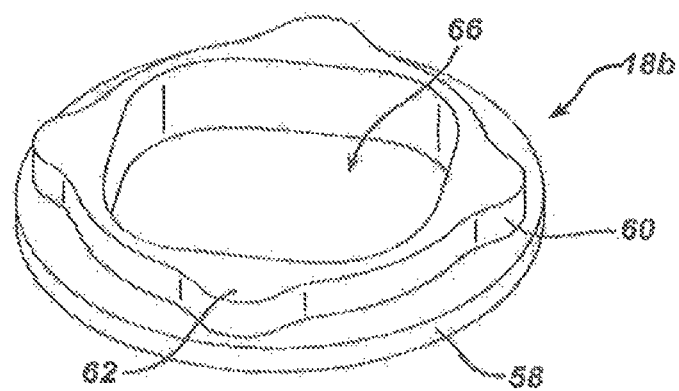
FIG. 5A is a perspective view of an embodiment of a locking mechanism that can be integrated within the bone screw described herein.
Figure 5B:
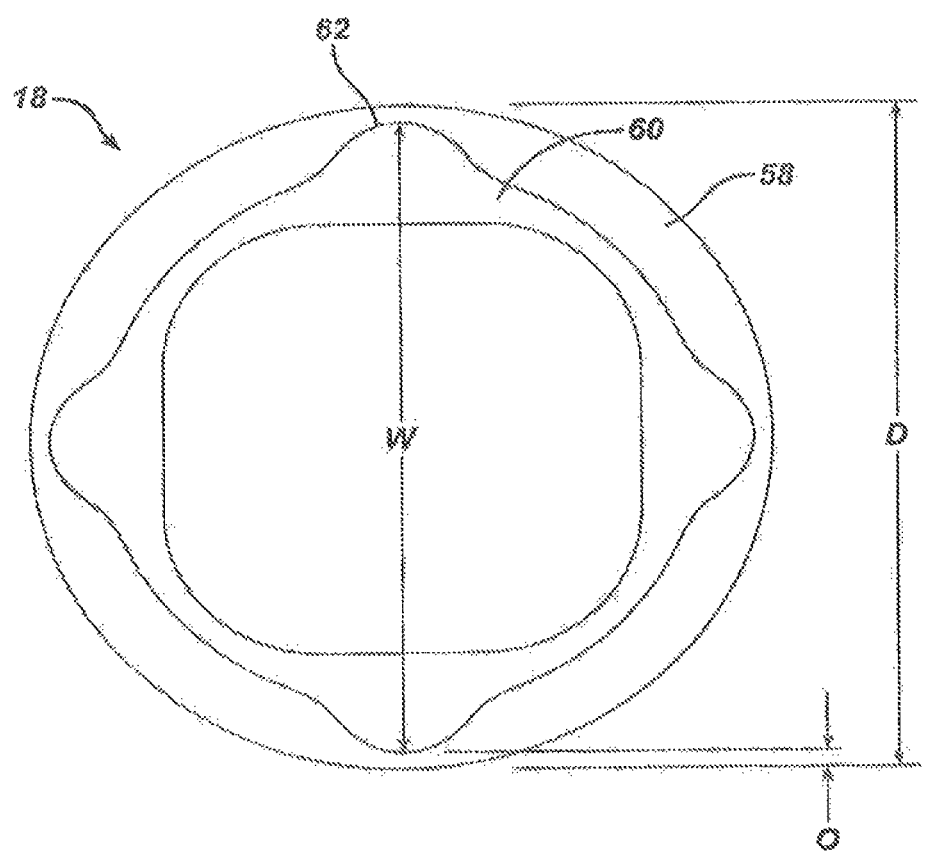
FIG. 5B is a top view of the locking mechanism of FIG. 5A.

In an alternative embodiment of the locking mechanism, locking mechanism 18b is a disc-like member that includes two portions, one that is seated within the bone screw head 36 and another that performs the locking function. FIGS. 5A and 5B illustrate an exemplary locking mechanism that includes a distal portion 58, which mates with bone screw head 36, and a proximal portion 60, which includes locking features such as protrusions 62. The distal portion 58 can be seated within a single groove 56 (FIG. 3) in such a way that the locking mechanism is able to rotate relative to the bone screw. In one example, the distal portion 58 can be generally circular in shape.

Locking mechanism 18b can also have a variety of alternative configurations. In one aspect, locking mechanism 18b could be inverted such that the proximal portion 60 of locking mechanism 18b mates with the bone screw head, and the distal portion 58 contains the locking features. In yet another aspect, the locking mechanism can be in the form of a member with a single portion that both mates with the bone screw head and includes locking features.

The relative size of proximal and distal portions 60, 58 can be adapted to permanently seat locking mechanism 18b within groove 56. For example, as shown in FIG. 5b, a maximum width W of proximal portion 60 can be slightly less than the diameter D of distal portion 58 to provide distal portion 58 with an offset O. The offset O defines the portion of distal portion 58 that extends into groove 56 and holds locking mechanism 18b within hollow interior 48. In one exemplary embodiment, the offset is in the range about 0.1 mm to 0.5 mm.

The maximum width of proximal portion 60 of locking mechanism 18b can be sized to contact wall 42 when the locking mechanism is rotated into the locked position. For example, proximal portion 60 can have a generally circular shape with protrusions 62 that form cam-like lobes. Protrusions 62 can be sized such that when they are in the locked position they abut inner surface 44 of wall 42 to either prevent the outer wall from radially deforming under a compressive force or to radially expand the outer wall. In an exemplary embodiment placing the locking mechanism in the locked position prevents the head from deforming (i.e., from deflecting inwardly). However, one skilled in the art will appreciate that the bone screw and locking mechanism can be configured such that the locking mechanism operates by causing an increase in the diameter of the head when it is placed in the locked condition, as discussed below.

The size of protrusions 62, is defined as the different between W, the maximum width of proximal portion 50 and the minor width of proximal portion (FIG. 5B). The size of protrusions 62 corresponds to the maximum amount of deflection which deflectable tabs 52 can achieve. In one embodiment, the protrusions 62 have a size in the range of approximately 0.2 mm to approximately 0.7 mm.

Figure 6A:
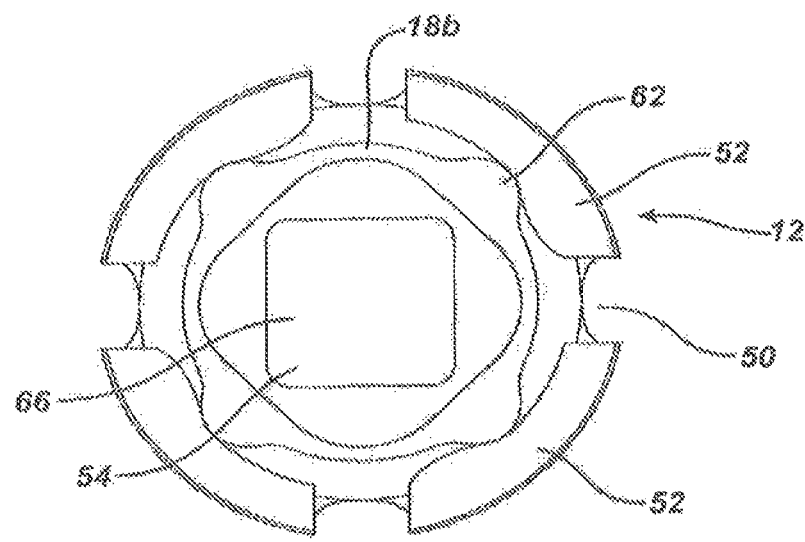
FIG. 6A is a top view of an embodiment a bone screw with a locking mechanism in a locked condition.
Figure 6B:
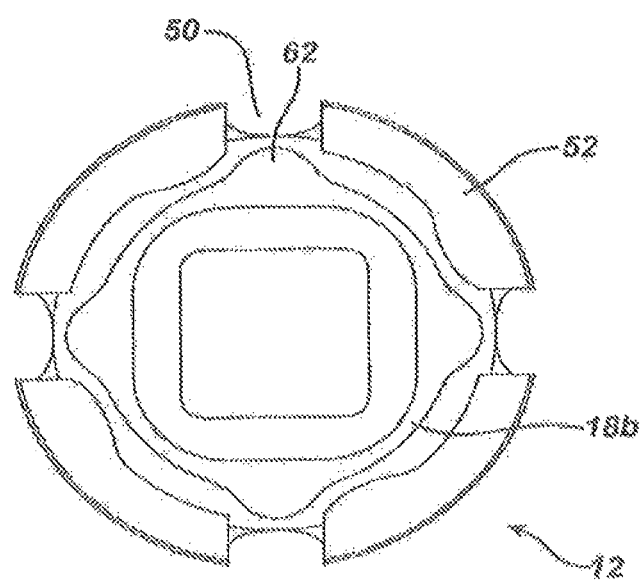
FIG. 6B is a top view of the bone screw of FIG. 6A with a locking mechanism in an unlocked condition.

FIG. 6A illustrates a bone screw head with locking mechanism 18b in the locked position. As shown, protrusions 62 are positioned in contact with deflectable tabs 52. In this position, the tabs 52 are prevented from deflecting in response to a compressive force due to the positioning of protrusions 62. The unlocked position can be achieved by rotating the locking mechanism such that the protrusions 62 are aligned with the slots 50 formed between deflectable tabs 52. In this position, shown in FIG. 6B, deflectable tabs 52 are free to deflect inwardly in response to a compressive force. As discussed above, in an exemplary embodiment, inward deflection of the tabs reduces the outer diameter of bone screw head 36 and allows the bone screw head to pass into aperture 16 through the top portion 22 thereof, which has a reduced diameter.

Locking mechanism 18b is dimensioned and positioned within the bone screw 12 such that when a compressive force is applied to bone screw head 36, the distal portion 58 of locking mechanism 18b does not interfere with the deformation of tabs 52. For example, diameter D of distal portion 58 can be such that that locking mechanism 18b is allowed some play within the groove 56. The diameter of the groove can be larger than diameter D of the locking mechanism disposed within the groove. The difference in the diameters allows some space between the outer edge of distal portion 58 and the inner surface of groove 56. When bone screw head 36 begins to deform, this space allows outer wall 42 to compress without immediately encountering, and being prevented from deforming by, the distal portion 58 of locking mechanism 18b.

As noted above, in another embodiment, locking mechanism 18a or 18b can be adapted to expand bone screw head 36 to lock bone screw head 36 within aperture 16. For example, locking mechanism 18b can be dimensioned such that the maximum width W of proximal portion 60 is larger than the internal diameter of the hollow interior 48. Rotating protrusions 62 into position behind tabs 52 would thus expand bone screw head 36 to occupy the larger central diameter 30 of aperture 16 and thereby prevent bone screw head 36 from passing through the top portion 22 of the aperture which has upper diameter 20. As discussed above, the magnitude of screw head deformation depends on the materials from which the bone screw is made and the size and/or intended use of the bone screw. In one aspect, the bone screw head can expand by approximately 0.1 to approximately 0.5 mm to lock the bone screw head in aperture 16.

Locking mechanism 18a or 18b can also include other features such as a drive feature adapted to mate with a complementary portion of a driver tool for shifting the locking mechanism between a locked and an unlocked position. For example, locking mechanism 18b can include a drive feature 66 adapted to receive a driver tool for rotating the locking mechanism between a locked and an unlocked position. As shown in FIGS. 5A through 6B, drive feature 66, like drive feature 54 in bone screw head 36 (FIG. 3), can be in the form of a female opening adapted to receive a drive element on a driver tool. For example, drive feature 66 can be a rectangular (e.g., square) opening that is centrally formed in the locking mechanism. One skilled in the art will appreciate that a variety of drive features can be used to rotate locking mechanism 18b. For example, drive feature 66 can be a female opening having a variety of other shapes (e.g., triangular, rectangular, hexagonal oval, irregular, etc) capable of mating with the driver element. Further, as discussed with respect to the drive feature 54 in bone screw head 36, the drive feature 66 can alternatively be configured as a male member that mates with a complementary female drive element on a driver tool.

In one embodiment, both the locking mechanism 18b and the bone screw head 36 can be adapted to receive a single driver tool for installing bone screw 12 within bone and rotating locking mechanism 18b between the locked and unlocked positions. For example, the drive feature 66 can be positioned coaxially with and proximal to drive feature 54, and it can be sized such that distal drive feature 54 can be accessed through the proximally positioned drive feature 66. A single driver tool can then access both drive features 54, 66 and perform the steps of implanting the bone screw and locking the locking mechanism without removing the driver tool. As such, a surgeon can implant the bone plate system with fewer steps while using fewer tools.

Figure 7A:
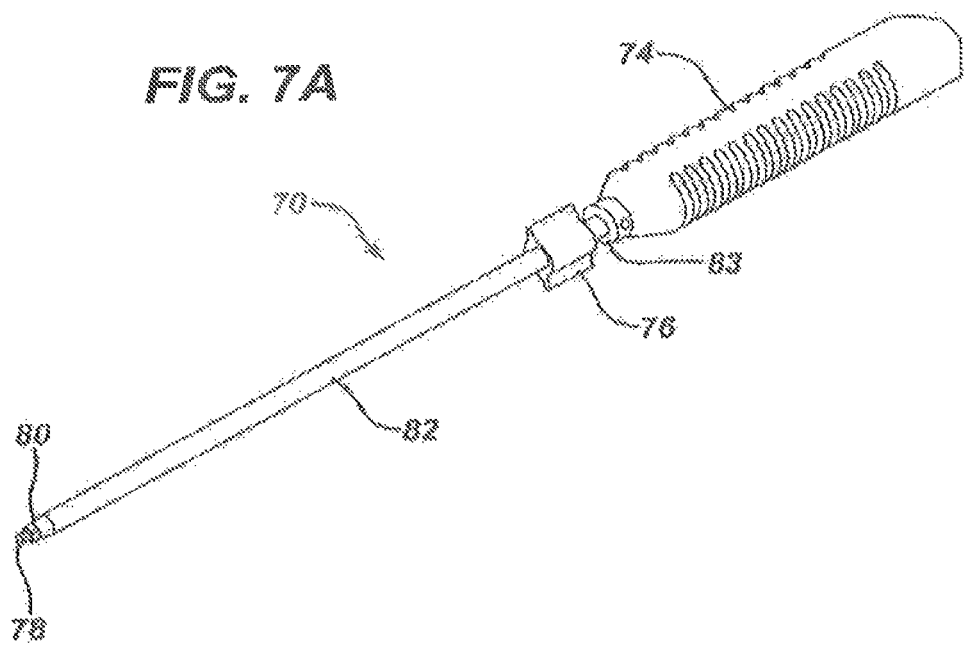
FIG. 7A is an embodiment of an installation/locking instrument useful with the bone plate system.
Figures 7B, 7C:
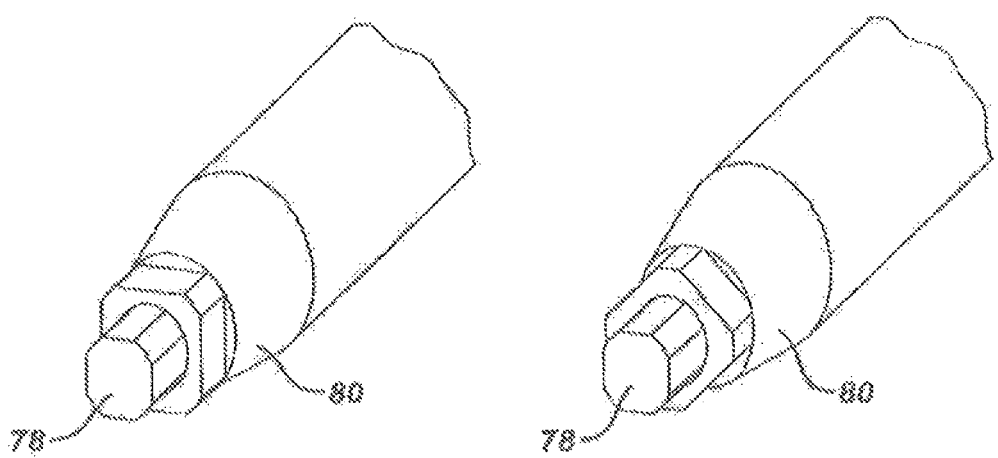
FIG. 7B is a perspective view of the distal end of the driver tool shown in FIG. 7A.
FIG. 7C is a perspective view of the distal end of the driver tool shown in FIG. 7A in an alternative configuration.

One such exemplary driver tool 70 is illustrated in FIGS. 7A through 7C. As shown driver tool 70 can include an elongate body having proximal first and second handle portions 74, 76 and corresponding distal first and second driver elements 78, 80 adapted to mate with drive feature 54 and drive feature 66, respectively. The driver elements 78, 80 are shaped and sized to mate with drive features 54, 66 of bone screw 12 and locking mechanism 18b, respectively. For example, the first mating portion 78 is shaped for insertion into the bone screw 12 (FIG. 3), while the larger, proximal mating portion 80 is adapted to mate with drive feature 66 of the locking mechanism.

In one embodiment, an outer body sheath 82 connects handle portion 76 and driver element 80. The outer body sheath 82 is positioned over shaft 83 which connects handle 74 to driver element 78. The bone screws can be installed by mating the driver element 78 with the drive feature 56 within the screw head. Rotation of the handle 74 will in turn cause the bone screw to rotate so that it can be driven into bone. Since neither the shaft 83 nor handle 74 is mechanically linked to sheath 82, rotation of handle 74 will not cause sheath 82 or driver element 80 to rotate. Once bone screw 12 is implanted, and bone screw head 36 is seated within aperture 16, a surgeon can then rotate only handle 76 on shaft 82 causing the driver element 80 to rotate independent of driver element 78, and lock the locking mechanism within the bone screw head.

FIGS. 7B and 7C illustrate the independent movement of the first and second mating portions that facilitate actuation of the locking member. For example, FIG. 7B shows the second driver element 80 in an unlocked position, while FIG. 7C shows the second driver element 80 rotated 45 degrees relative to the first driver element 78 to rotate locking mechanism 18b into a locked position.

To assist with locking the locking mechanism, a visual indicator or a stop can signify when the locking mechanism is positioned in the locked position. For example, a marker on the locking mechanism could be positioned to line up with a corresponding marker on the bone screw head when the locking mechanism is rotated into the locked position. In use, a surgeon would line up the markers to lock the bone screw in the aperture. A pair of markers could alternatively be positioned on driver tool 70 to indicate the relative position of driver element 78, 80 and thus the locked or unlocked condition of bone screw 12. In another embodiment, a stop could be placed inside the bone screw head to prevent rotation of the locking mechanism past the locked position. The stop, for example, could allow rotation of the locking mechanism from an unlocked position to an adjacent locked position, but not allow the locking mechanism to rotate further. In another embodiment, the stop can be located in the driver tool to limit rotation of the outer sheath relative to the inner shaft. Rotation of driver element 78 relative to driver element 80 could then be limited to movement between an unlocked and an adjacent locked position.

One skilled in the art will appreciate that multiple driver tools can also be used with bone screw 12. For example, a first driver tool adapted can be adapted to mate with drive feature 54 for implanting the bone screw, while a second driver tool can be adapted for mating with drive feature 66 for locking the bone screw in position.

The bone plate system 10, as disclosed herein, can include a variety of bone screw/bone plate kinematics. For example, bone plate 1 and bone screw 1 can be adapted such that when bone screw 12 is locked in bone plate 14, the bone screw is rigidly fixed and movement of the screw in any direction is prevented. The bone plate system can also be of a semi-rigid type in which after a screw locking mechanism is engaged, screw backout is prevented, but the screw is able to move in all directions polyaxially). Further, the bone plate system can also be of a hybrid type in which after the screw locking mechanism is engaged, screw backout is prevented, but the screw is able to move in only one selected direction (e.g., the superior-inferior or the transverse direction). Moreover, the bone screws may translate within an aperture of a plate. For example, a bone screw may translate along the length of an elongated slot defining an aperture in the plate.

The components of the exemplary bone plate systems described herein may be constructed of any biocompatible material including, for example, metals, such as stainless steel and titanium, polymers, and composites thereof. In certain exemplary embodiments, the bone plate system may be constructed of a bio-resorbable material, such as, for example polylactic acid (PLA) and polyglycolic acid (PGA), and blends or copolymers thereof.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed as new and desired to be protected by Letters Patent of the United States is:

1. A bone screw, comprising:
    an elongate member having a threaded shank, and a head at a proximal end thereof, the head being radially deformable and being defined by an outer wall defining an inner hollow region, at least one seating groove being formed in an inner surface of the outer wall; and
    a screw locking mechanism at least partially disposed in the head, the screw locking mechanism being rotatable within the head between a locked condition and an unlocked condition, the screw locking mechanism being at a same axial location with respect to the head along a longitudinal axis of the head while in the locked condition and in the unlocked condition;
    wherein the locking mechanism has a substantially circular shaped first portion adapted to be rotatably disposed within the seating groove, and a second portion that includes at least one locking feature that is adapted to engage the inner surface of the outer wall when the screw locking mechanism is in the locked condition and not engage the head when the screw locking mechanism is in the unlocked condition, and
    wherein the head in the locked configuration is radially deformed from the head in the unlocked configuration.

2. The bone screw of claim 1, wherein the head has at least one axially oriented slot formed in the outer wall and extending into the hollow region.

3. The bone screw of claim 2, wherein the head has an outer diameter that is greater than a major diameter of the shank.

4. The bone screw of claim 2, wherein the head has four slots.

5. The bone screw of claim 4, wherein the locking mechanism has four locking features.

6. The bone screw of claim 5, wherein the locking features are cam-like lobes.

7. The bone screw of claim 6, wherein in the locked condition the locking features engage an inner surface of the outer wall of the head to prevent deformation of the head.

8. The bone screw of claim 7, wherein in the unlocked condition the locking features align with the slots to permit deformation of the head.

9. The bone screw of claim 2, wherein at least a portion of the outer wall of the head has a spherically shaped outer surface.

10. The bone screw of claim 2, wherein the outer wall of the head has a tapered upper portion and a tapered lower portion.

11. The bone screw of claim 1, wherein the seating groove extends circumferentially about the inner surface.

12. The bone screw of claim 1, wherein the head has a drive feature formed at a distal portion of the inner hollow region.

13. The bone screw of claim 12, wherein the locking mechanism has a drive feature.

14. The bone screw of claim 13, wherein the drive feature in the locking mechanism and the drive feature in the head are coaxial.

15. The bone screw of claim 13, wherein the drive feature in the locking mechanism is a rectangular female opening having an area larger than the area of the drive feature of the head.

16. The bone screw of claim 12, wherein the drive feature in the head is a rectangular female opening.

17. The bone screw of claim 1, wherein threads are disposed on an inner surface of the outer wall.

18. A bone screw, comprising:
    an elongate member having a threaded shank, and a head at a proximal end thereof, the head being radially deformable and being defined by an outer wall defining an inner hollow region, and the head having a groove formed in the inner hollow region thereof; and
    a screw locking mechanism that is rotatable within the head between a locked condition and an unlocked condition, the screw locking mechanism including a distal disc-shaped lip seated within the groove when the screw locking mechanism is in the locked condition and when the screw locking mechanism is in the unlocked condition, such that the screw locking mechanism is at a same axial location with respect to the head along a longitudinal axis of the head while in the locked condition and in the unlocked condition, and the screw locking mechanism including a proximal portion including a protrusion proximal to the lip that is configured to engage the head when the screw locking mechanism is in the locked condition and not engage the head when the screw locking mechanism is in the unlocked condition; and wherein the maximum width of the proximal portion is larger than the internal diameter of the inner hollow region when the screw locking mechanism is in the unlocked condition.

19. A bone screw, comprising:

an elongate member having a threaded shank, and a head at a proximal end thereof, the head being radially deformable, the head being defined by an outer wall defining an inner hollow region, and the head having a channel formed in the inner hollow region thereof; and a screw locking mechanism having proximal and distal portions, a maximum width of the proximal portion being smaller than a maximum width of the distal portion, the distal portion being at least partially disposed in the channel formed in the head and being rotatable therein, the head being in a first configuration when the proximal portion of the screw locking mechanism is in a first position relative to the head, the head being in a second configuration when the proximal portion of the screw locking mechanism is in a second position relative to the head, the second position being rotated from the first position about a longitudinal axis of the shank, and the head in the first configuration being radially deformed from the head in the second configuration;

wherein the screw locking mechanism is at a same axial location with respect to the head along a longitudinal axis of the head when the head is in first configuration and when the head is in the second configuration.

\* \* \* \* \*